United States Patent [19]

Fein et al.

[11] 3,954,682

[45] May 4, 1976

[54] INSOLUBLE POROUS POLYMERIC-PHENOLIC COMPLEXES

[75] Inventors: Marvin M. Fein, Westfield, N.J.; Nathan D. Field, Allentown; Earl P. Williams, Pen Argyl, both of Pa.

[73] Assignee: GAF Corporation, Wayne, N.J.

[22] Filed: Jan. 25, 1974

[21] Appl. No.: 436,608

Related U.S. Application Data

[63] Continuation of Ser. No. 25,249, April 2, 1970, abandoned.

[52] U.S. Cl. .............................. 260/2.5 B; 162/161; 210/64; 210/501; 260/46.5 UA; 260/47 UP; 260/78 P; 260/78.5 B; 260/79.7; 424/49; 424/78; 424/80; 426/330.3; 426/330.4; 426/335; 426/532; 526/23; 526/54; 526/260; 526/264; 526/310

[51] Int. Cl.$^2$............................................. C08J 9/00

[58] Field of Search........ 260/2.5 B, 47 UP, 80.3 N, 260/88.3 L

[56] References Cited

UNITED STATES PATENTS

| | | | |
|---|---|---|---|
| 2,941,980 | 6/1960 | Robinson | 260/88.3 L |
| 3,235,490 | 2/1966 | Goren | 260/80.3 N |
| 3,689,439 | 9/1972 | Field et al. | 260/2.5 N |

*Primary Examiner*—Richard B. Turer
*Attorney, Agent, or Firm*—Walter C. Kehm

[57] ABSTRACT

Phenolic complexes of water-insoluble but water-swellable crosslinked N-vinyllactam or N-alkyl-N-vinylamide polymers in the form of porous beads or granules and a process of preparing same. The complexes are particularly suited for use in situations wherein phenolic materials in limited quantities are desired such as, for example, in canisters or columns which are used to treat liquids or water. The novel complexes are prepared by adsorbing a phenolic material onto the porous granular or porous bead-like crosslinked N-vinyllactam or N-alkyl-N-vinylamide polymers.

4 Claims, No Drawings

INSOLUBLE POROUS POLYMERIC-PHENOLIC COMPLEXES

This is a continuation of application Ser. No. 25,249, filed Apr. 2, 1970, now abandoned.

The instant invention is directed to novel phenolic-polymeric complexes. In particular, the instant invention is directed to novel phenolic-crosslinked N-vinyllactam or N-alkyl-N-vinylamide polymers in the form of porous beads or porous granules.

For many years water insoluble powders of polyvinyl pyrrolidone, similar lactams, and similar vinylamides were utilized for a variety of purposes including among others as filtering media in packed column and similar filtration purification systems. The powdered materials, however, are unsatisfactory in most instances because of the extremely long drainage time of liquid through the powder. Accordingly, it has long been the desire to provide an improved product which will eliminate such deficiency.

Co-pending application Ser. No. 736,302, filed June 12, 1968 now U.S. Pat. No. 3,689,439, describes such an improved product, the product being a crosslinked vinyl pyrrolidone or similar polymer in the form of highly porous beads which are water-insoluble but water-swellable. As disclosed in such co-pending application, such novel crosslinked polymers have the advantage of good strength and rapid throughput in gravity or pressure filtration systems or packed column filtration operations.

According to the instant invention, it has been found that new products may be prepared through the preparation of phenolic complexes of water-insoluble but water-swellable crosslinked N-vinyllactam or N-alkyl-N-vinylamide polymers in the form of porous beads or porous granules. In this connection, it has been found in accordance with the instant invention that such porous bead-like phenolic complexes are of particular use in a wide range of applications and, in particular, in those applications wherein a phenolic material is desired but in limited quantity. That is to say, that the porous polymeric granules of the instant invention as a result of the complexing with phenolic materials establish an equilibrium characteristic which beneficially releases said phenolic material in limited quantities. Therefore, said materials are ideally suited for use in canisters and/or columns where they may be used either to treat liquids an/or water or in processes wherein liquids are treated by diffusion through the bead bed. In such processes, release of the phenolic material of the complex may be regulated through control of the equilibrium relationship and the flow rate of the liquid therethrough.

Therefore, it is an object of the instant invention to provide a novel complex which is particularly suited for use in applications wherein quantities of phenolic material are necessary.

A still further object of the instant invention is to provide a phenolic complex with a water-insoluble but water-swellable crosslinked N-vinyllactam or N-alkyl-N-vinylamide polymer in the form of porous beads or porous granules.

Yet another object of the instant invention is to provide a process for preparing phenolic complexes of a water-swellable crosslinked porous N-vinyllactam or N-alkyl-N-vinylamide bead or granule polymers.

These and other objects of the instant invention will be more evident from the following more detailed description thereof.

As previously noted, the present invention is directed to a phenolic complex of a water-insoluble but water-swellable crosslinked N-vinyllactam or N-alkyl-N-vinylamide which polymeric material is in the form of either porous beads of porous granules.

The N-vinyllactams employed in the preparation of the crosslinked polymers of the phenolic complexes of the present invention are lactams corresponding to the general formula:

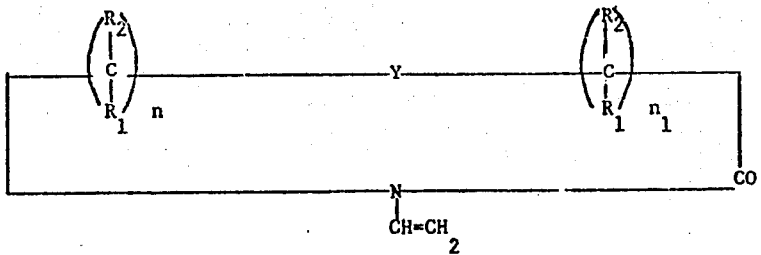

where $R_1$ and $R_2$ = hydrogen, alkyl and aryl

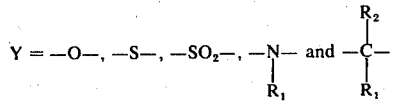

$n$ and $n_1$ range from 0 to 5 but where only one of the n or $n_1$ values may be zero.

Such N-vinyllactams are those which can be prepared, for example, by the vinylation of lactams such as disclosed in U.S. Pat. Nos. 2,891,058; 2,265,450; 2,334,454 and 3,097,087. Similarly, the N-vinyl lactams may be prepared in a known manner by N-vinylation of the corresponding lactams at elevated temperatures in a manner such as disclosed in U.S. Pat. No. 2,317,084. Accordingly, representative N-vinyl lactams operable in accordance with the present invention include such as : N-vinyl-2-pyrrolidone and N-vinyl-substituted derivatives of the following lactams: 3,3-dimethyl-2-pyrrolidone, 4,4-dimethyl-2-pyrrolidone, 3,4-dimethyl-2-pyrrolidone, 3-ethyl-2-pyrrolidone, 3,5-dimethyl-2-pyrrolidone, 3-phenyl-2-pyrrolidone, 4-acryl-2-pyrrolidone, 5-ethyl-2-pyrrolidone, 3-methyl-2-pyrrolidone, 4-methyl-2-pyrrolidone, 5-methyl-2-pyrrolidone, 3,3,5-trimethyl-2-pyrrolidone; 2-piperidone, 5,5-diethyl-2-piperidone, 5,6-dimethyl-2-piperidone, 4-ethyl-2-piperidone, 6-ethyl-2-piperidone, 6-ethyl-3-methyl-2-piperidone, 3-methyl-2-piperidone, 4-methyl-2-piperidone, 5-methyl-2-piperidone, 6-methyl-2-piperidone; 2-caprolactam, 3,6-dimethyl-2-caprolactam, 4,6-dimethyl-2-caprolactam, 4,7-dimethyl-2-caprolactam, 7,7-diethyl-2-caprolactam, 3-ethyl-2-caprolactam, 5-ethyl-2-caprolactam, 6-ethyl-2-caprolactam, 7-ethyl-2-caprolactam, 4-ethyl-6-methyl-2-caprolactam, 6-ethyl-4-methyl-2-caprolactam, 3-methyl-2-caprolactam, 4-methyl-2-caprolactam, 5-methyl-2-carprolactam, 6-methyl-2-caprolactam; 2-oxazinidinone (e.g. U.S. Pat. No. 2,905,669 and U.S. Pat. No. 3,097,087), 5-ethyl-2-oxazinidinone, 5-phenyl-2-oxazinidinone, 4,5-dimethyl-2-oxazinidinone, 5,5-dimethyl-2-oxazinidinone, 2,5-diphenyl-2-oxazinidinone, 2-phenyl-4-oxothiazolidone, 2,2'-diphenyl-4-oxothiazolidone, 2,2'-dimethyl-4-oxothiazolidone; 2-oxazolldinone (deriv. in U.S. Pat. No. 2,905,690 and U.S. Pat. No. 2,891,058), 5-methyl-2-oxazolidinone, 4-methyl-2-oxazolidinone, 5-ethyl-2-oxazolidinone, 4,5-dimethyl-2-oxazolidinone, 2-phenyl-2-oxazolidinone, 5-butyl-2-oxazolidinone, 5-propyl-2-oxazolidinone, 4,5-diethyl-2-oxazolidinone; 3-morpholinone disclosed in U.S. Pat. No. 2,987,509, e.g., 5-methyl-3-morpholinone, 5-ethyl-3-morpholinone; 3,5-dimethyl-3-morphilinone; 2-piperazinone (e.g. JACS 62, 1202 (1940)), the 3,3-dimethyl-2-ketopiperazine, 3-methyl-2-ketopiperazine; 4-thiazolidone (e.g. JACS 76, 578 (1954)), 2-methyl-4-thiazolidinone; 2-phenyl-4-thiazolidinone; 2-phenyl-4-thiazolidinone dioxide; 2-thiazolidone (J. Chem. Soc. 1949, 2367); 3-thiamorpholinone; 2-pyrimidone (e.g., J. Chem. Soc. 1959, 525); 2-imidazolidones (e.g. Ann. 232, 1222 (1885 )); N,N-ethylene-thioureas (e.g. J. Biol. Chem. 163, 761 (1946); tetrahydro-(2H, 1, 3)-oxazin-3-ones (e.g., U.S. Pat. No. 2,940,971), and the like.

Similarly, suitable N-alkyl-N-vinylamides useful in accordance with the present invention are those which correspond to the formula:

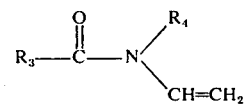

wherein $R_3$ and $R_4$ are independently selected from the class of hydrocarbon radicals of 1 to 4 carbon atoms preferably 1 to 2 carbon atoms.

Such N-alkyl-N-vinylamides are illustrated in U.S. Pat. No. 3,214,370, exemplary amides being: N-methyl-N-vinylacetamide, N-ethyl-N-vinylacetamide, N-butyl-N-vinylacetamide, N-methyl-N-vinylpropionamide, N-methyl-N-vinylpentanoic acid amide, N-methyl-N-vinylformamide and the like.

In preparing the porous granular or porous bead form of polymer in accordance with the present invention, the N-vinyllactam or N-alkyl-N-vinylamide, with or without a further copolymerizable monomer and with a crosslinking agent as to be hereinafter defined, is polymerized in a manner described in co-pending applications Ser. No. 736,302 filed June 12, 1968 U.S. Pat. No. 3,689,439 and Ser. No. 875,516 filed Nov. 10, 1969 now abandoned. In this connection, as defined in such co-pending applications the porous granular or bead form of the polymer is produced from a suspension polymerization system wherein the lactam or amide monomer with optional copolymerizable monomer and crosslinking agent is polymerized in an aqueous solution of an electrolyte, the suspension being maintained during polymerization by mechanical means. In such polymerization process a free radical polymerization source is utilized.

In this regard, the preparation of the porous bead or porous granular form of polymer involved the polymerization of the N-vinyl lactam or N-alkyl-N-vinylamide with an amount of crosslinking agent, i.e., divinyl monomer within the range of about 0.1 to about 20% by weight based on the weight of the N-vinyl lactam or N-alkyl-N-vinylamide. Such polymerization is carried out in an aqueous solution of an electrolyte, the concentration of electrolyte being high enough to produce phase separation before or during polymerization. In this regard, a preferred electrolyte solution contains from about 10 to about 20% sodium sulfate. Since the monomers polymerized in accordance with this procedure are not very soluble in such electrolyte solutions, by using more than enough monomers to saturate the solution of electrolyte a suspension of the excess monomers can be made through mechanical agitation. In this connection, the use of excess undissolved salt is often beneficial since the solid becomes enmeshed in the bead or granule and upon dissolution increases the surface area of the porous product.

In the polymerization process, the relative proportion of total monomer to water is determined at the upper limit by the ability of heat removal and the danger of particle agglomeration, this upper limit being as high as about 80% monomer, preferably about 50% monomer based upon the weight of the water. The lower limit is inter alia based on convenience of operating without undue bulk, the process of the present invention being capable of being carried out successfully with as low as 1% monomer, preferably 10% monomer based on the weight of the water in the aqueous electrolyte system.

As indicated previously, the polymerization process is conducted in the presence of a catalyst which provides a source of free radicals. In this respect, any of the conventional free radical initiator catalysts generally employed in vinyl polymerizations can be employed in accordance with the process of the present invention, such catalysts being added either to the mixture of monomers polymerized in accordance with the present invention or to the aqueous solution of electrolyte. Thus, for example, the catalyst can comprise any of the conventional peroxide catalysts, e.g., benzoyl peroxide, di-t-butyl peroxide, as well as the preferred azo catalysts, e.g., azobisisobutyronitrile.

The crosslinking agents which are suitably employed in the preparation of the porous bead or porous granular form of polymer in accordance with the present invention are those which contain two or more functional groups capable of taking part in the polymerization reaction so as to provide a polymeric product having a crosslinked or three dimensional structure.

Accordingly, suitable crosslinking agents that have been found particularly applicable in accordance with the present invention are the alkylenebisacrylamides, e.g., N,N'-methylenebisacrylamide, the alkylene glycol dimethacrylates, e.g., ethylene glycol dimethacrylate, diethylene glycol dimethacrylate, tetraethylene glycol dimethacrylate, higher polyethylene glycol dimethacrylate, 1,3- and 1,4-butanediol diacrylates and dimethacrylates, etc. and the divinyl aromatic compounds, e.g., divinyl benzene, divinylethylbenzene, divinylchlorobenzene, divinyltoluene, divinyl naphthalene, etc. Other suitable crosslinking agents include allyl acrylate, p-isopropenylstyrene, trivinyl meseate, diallyl maleate, divinyl ether, 1,3- or 1,4-divinyl oxybutane, trivinyl citrate, divinyl o-phenylene diacetate, vinyl allyl ether, diethylene glycol diallyl ether, trivinyl glyceryl ether, divinyl glyceryl ether, tetravinyl pentaerythrityl ether, hexahydro-1,3,5-triacryl-s-triazine, vinylpyrrolidone dimers described in U.S. Pat. No. 3,252,995, and the like. Additionally, mixtures of the above-cited suitable crosslinking agents can be advantageously employed where desired.

As indicated above, the crosslinking agent is generally employed in an amount of from about 0.1 to about 20% by weight based upon the weight of the N-vinyl lactam or N-alkyl-N-vinylamide monomer. An amount of from about 3 to about 5% of the crosslinking agent is preferred.

Similarly, as indicated above, the N-vinyl lactam or N-alkyl-N-vinylamide can be polymerized in the presence of an optional copolymerizable monomer. Preferably such copolymerizable monomer should be present in an amount of less than about 50% by weight based on the weight of the N-vinyl lactam or N-alkyl-N-vinylamide monomer, and more preferably, in an amount of less than about 20% by weight.

Examples of comonomers which can be employed are the N-vinyllactams or N-alkyl-N-vinylamides listed above, or acrylates e.g., methyl, ethyl, propyl and higher akyl, phenyl, naphthyl and other aryls; α-substituted acrylates such as α-methyl, ethyl, propyl and higher alkyl, phenyl, naphthyl and other aryls; vinyl ethers, e.g., methyl, ethyl, propyl and higher alkyls, acrylamide, acrylic acid, acrylonitrile, allyl acetate, allyl alcohol, crotonic acid, dimethylaminoethylvinyl sulfide, diethylhexyl maleate, didodecyl maleate, fumaramide, itaconic acid, methacrylic acid, methacrylamide, methoxy styrene, methyl vinyl ketone, methyl vinylpyrrolidone, 2-methyl-5-vinylpyridine, styrene trichloroethylene, vinyl carbazole, vinylimidazole, vinyl laurate, vinyl methyl benzimidazole, vinyl methyl dichloro silane, vinyl methyl oxazolidinone, vinyl oxyethylurea, vinyl propionate, vinyl pyridine, vinyl siloxanes, vinyl stearate, vinyl acetate (and the derived vinyl alcohol).

It is noted that a further description of the production of the crosslinked particulate polymeric N-vinyllactam polymers and copolymers and N-alkyl-N-vinylamide polymers and copolymers in the forms of porous beads or porous granules can be found in above referenced co-pending applications Ser. Nos. 736,302 and 875,516. Thus, for example, the polymerization process may be carried out by adding all of the monomers to the salt solution in one charge or such monomers may be added in portions or continuously during the polymerization. The polymerization is usually carried out at about 50 to 80°C and requires a relatively short time for completion, e.g., about two to six hours. Accordingly, the disclosure of said co-pending application Serial No. 736,302 as it pertains to the production of the water-insoluble but water-swellable porous bead-like crosslinked polymers employed in the process of the present invention is herein incorporated by reference.

The above-discussed porous granular or porous bead-like crosslinked N-vinyllactams or N-alkyl-N-vinylamides according to the instant invention are then complexed with the phenolic material. The phenolic material employed in connection with the instant invention may be any soluble compound, i.e., water or organic liquid soluble containing a phenolic hydroxyl group. Therefore, the compounds which may be employed in forming the complexes of the instant invention are extremely wide in scope and not amenable to a simplified listing thereof. It is to be noted, however, that the following materials are merely representative thereof and in no way limiting on the scope of phenolic material which may be employed in connection with the complexes of the instant invention. Such phenolic materials may be exemplified by:

Phenol
resorcinol
hydroquinone
salicylic acid
nonylphenol
p-cresol
8-hydroxyquinoline
8-hydroxyquinoline hydrochloride
citric acid
4-nitrophenol
phloroglucinol
dichlorophene
gallic acid
1,5-dihydroxynaphthalene
pyrogallol
catechol
hexachlorophene
o-chlorophenol
4-chloro-o-cresol
3-aminophenol
butyl hydroxyanisole
2-nitrophenol
n-heptyl-p-hydroxy benzoate
2,6-di-tert-butyl-p-cresol
2-hydroxy-4-methoxy-benzophenone-5-sulfonic acid
2,4-dihydroxy benzophenone
2-hydroxy-4-methoxy-benzophenone
2,2'-dihydroxy 4,4'-dimethoxy-benzophenone
2,2',4,4'-tetrahydroxy benzophenone
sodium 2,2'-dihydroxy-4,4'-dimethoxy-5-sulfo-benzophenone
o-cresol
m-cresol
and the like.

The novel complexes of the instant invention may readily be formed by contacting the crosslinked porous bead or porous granule N-vinyllactam or N-alkyl-N-vinylamide polymers with the phenolic material. That is to say, the phenolic material may be dissolved in a suitable solvent or mixture of solvents therefor in varying solution concentrations over a wide range which is subject only to the desired use of the end product. The solvent employed in the process of the instant invention would, of course, be one in which the phenol material is soluble. The amounts employed in connection therewith are not in anyway critical or limited hereby.

The novel phenolic complexes of water-insoluble but water-swellable porous bead or porous granule crosslinked N-vinyllactams or N-alkyl-N-vinylamide polymers as noted are ideally suited for use in applications wherein a limited amount of phenolic material is desired. For example, it has been found that finished beer to which 10 to 12 parts per million of N-heptyl-p-hydroxy benzoate was added, was found to be microbiologically stable. It is noted, however, that an elaborate control system is needed for the addition of said n-heptyl-p-hydroxy benzoate so as to guard in commercial installations against the precipitation of said n-heptyl-p-hydroxy benzoate in the beer and further the loss of the ratio control of additive solution flow rate to beer flow rate. The former is important because at the pH values of the beer, the additive N-heptyl-p-hydroxy benzoate tends to precipitate from the additive solution. The latter ratio is important because it would result in a beer being either over or under treated depending upon the variables in said rate. Therefore, one of the particular uses to which the novel polymeric materials of the instant invention can be put would be to incorporate a n-heptyl-p-hydroxy benzoate complex, crosslinked N-vinyllactam or N-alkyl-N-vinylamide polymer in porous granular or porous bead form into a canister which would be designed to be inserted into the finished beer process. With use of such a phenolic complex, one would eliminate the need to solubilize the additive material by raising the pH for example. Furthermore, since the additive material normally must be employed in solution which can be effected only at a pH at which pH the ester linkage therein is hydrolyzed, one would also have the added advantage of being able to store the usable canisters or columns over an extended period of time whereas with solutions of n-heptyl-p-hydroxy benzoate, such storage is not possible. Further uses of the instant invention include the storage of phenolic complexes of polymeric porous granules in canisters or cartridges which porous granules are complexed with phenolic pesticides. Such canisters or cartridges may then be employed by attaching same to hoses, sprays, or other water sources wherein a controlled dilution would be effected. Such use of pesticides would, of course, overcome the numerous difficulties presently associated with the dilution of such pesticide materials prior to the use thereof. Furthermore, it is noted that the use of such canisters or cartridges would inherently control the amount of pesticide material applied and therefore avoid mistakes in such dilution. Furthermore, an indicator dye may, of course, be incorporated into said canisters or cartridges in the bead bed per se so as to visably demonstrate the presence or absence of pesticide material and the relative use thereof.

An example of the above use of the novel phenolic complexes of the instant invention is a polymeric porous granule containing 4,6-dinitro-o-sec-butylphenol in a cartridge attached to a garden hose. Such a phenolic complex would be effective for the control of mites, insects and weeds. It is also noted that the porous granules would be effective against the same pests if applied as a dry granule to the soil. In such dry use, one would incorporate a dye material into said granules so as to indicate the areas covered by said granules to the user. A further advantage of the dry granules would be that the chemical release would be prolonged and diminished during dry spells when damage could be caused by an excess thereof and increased during wet spells, which periods are also the most advantageous for weed growth.

A still further use of the novel phenolic materials of the instant invention would be in the field of industrial waste treatment and sewage treatment. For example, granules containing trichlorophenol could be employed as slimicides in paper mills. Further industrial uses of the novel complexes of the instant invention are in circulating systems or storage vats as bacteriostats and algicides. For example, canisters of porous granules treated with 2,2'-thiobis(4,6-dichlorophenol) would be effective as preservatives in cutting oils and as algicides in water treatment. 2,6-di-tert-butyl-p-cresol and butyl hydroxyanisole could also be complexed according to the instant invention and be employed in granular form as antioxidants.

In the field of home sanitation, the novel phenolic porous granular complexes of the instant invention could be employed as sanitary germicides for the maintenance of toilet bowls. In such a use, phenolic materials such s phenol or guaiacol could be complexed according to the process of the instant invention.

In the field of oral hygiene, a phenolic complex of 4-n-hexyl resorcinol could be prepared with the resulting porous beads being incorporated into a small cartridge. When such a cartridge is held under tap water, a disinfectant or mouth wash is instantly provided. Cartridges containing disinfectants, tonics and antibiotics can be inserted in automatic drinking systems for poultry and cattle in a manner similar to the above. Such phenolic materials also include, oxytetracycline, chlortetracycline and saligenin.

Fungicidal materials such as 8-hydroxyquinoline or dichlorophene can be complexed within the scope of the instant invention so as to provide a porous bead or porous granular-like product which would release same. Dry granules may also be prepared which slowly release air attractants, repellents or fragrances. For example, eugenol or isoamyl salicylate may be employed as attractants in poison baits for moths and flies. Creosote may be employed as a barrier to the migration of Chinch bugs. Salicylaldehyde or vanillin may be employed as fragrances in room deodorant and other similar compositions.

The particle size of the porous granules or porous beads which result according to the process of the instant invention is not considered particularly critical thereto. It is to be noted, however, that said phenolic complexes having a 16 – 60 mesh size (U.S. Standard Sieve Series) are considered particularly well suited for use in canisters and/or columns.

The instant invention will now be illustrated by means of the following more detailed examples thereof. It is to be noted, however, that the instant invention is not deemed as being limited thereby.

EXAMPLE 1

Into a 2-gallon, stainless steel stirred autoclave the following ingredients were charged: 3.3 g. azobisisobutyronitrile previously dissolved in 660 g. of vinyl pyrrolidone; 33 g. Dow divinylbenzene mixture (50–60; Assay 55%); 2150 g. distilled water; 10 g. 10% by weight dibasic sodium phosphate buffer solution; 570 g. anhydrous sodium sulfate (Baker's Reagent Grade).

The autoclave was then purged of air by applying a vacuum to 25 mm. The vacuum was then released with nitrogen and the procedure repeated two more times. The materials were then heated with stirring (210 RPM, 4 blade turbine) to 65°C over a period of one hour and held at said temperature for a period of three hours at a pressure of 3 to 4 Psig. A side flange was removed from the autoclave, and a dispersion of 1.5 g. azobisisobutyronitrile in 50 mls. of C.P. ethanol were added through the port. The flange was then replaced and the reaction continued for an additional hour at 65°C. The temperature was then raised to 85°C over a period of one-half hour and then held at that temperature for an additional two-hour period (8 to 10 Psig). The reaction product was then cooled and discharged into a Buchner funnel and washed with distilled water to remove any remaining sodium sulfate until a portion of the filtrate was tested with a few millimeters of saturated barium chloride solution and was found to be less turbid than a barium chloride control test with tap water. After allowing the excess water to drain, the wet porous beads weighed 3125 grams. A 100 gram portion of these porous beads were then dried in a high-vacuum oven at a temperature of between 65° and 70°C, and the dried porous beads again weighed, so as to determine a 95.1% yield.

EXAMPLE 2

Into a 500 ml. resin flask equipped with thermometer, stirrer, gas inlet, dropping funnel, and condenser connected to gas outlet were charged:

| | | |
|---|---|---|
| 40.0 | g. | (0.36 mole) distilled vinylpyrrolidone |
| 0.12 | g. | azobisisobutyronitrile |
| 240.0 | g. | distilled water |
| 1.6 | g. | (0.010 mole) methylenebisacrylamide |
| 0.46 | g. | 10% by weight $Na_2HPO_4$ solution |
| 40.0 | g. | anhydrous sodium sulfate |

Air was removed by closing the gas inlet and applying enough vacuum at the gas outlet to cause violent ebullition for 30 seconds. The vacuum was then released by allowing nitrogen to enter the gas inlet. This procedure was repeated two more times and then a positive pressure of nitrogen maintained by connecting the gas outlet to a mineral oil blow-out let having a depth of one inch of oil. The flask was heated with stirring in a constant temperature bath for 4 hours at a reaction temperature of 50° to 65°C. At the end of this time a solution of

| | | |
|---|---|---|
| 0.04 | g. | azobisisobutyronitrile |
| 0.4 | g. | methylenebisacrylamide |
| 10.0 | g. | C.P. ethanol |
| 10.0 | g. | distilled water | was charged to the dropping funnel and the air removed by violent ebullition and replaced with nitrogen. This procedure was repeated two more times by suitable adapters connected to the dropping funnel.

The above solution was then added to the contents of the flask and the heating continued for 2 additional hours at 62° to 65°C. At the end of this time the beads produced were filtered and washed with one gallon of distilled water and then dried in a vacuum oven at 40°C.

The dried white porous beads weighing 41.5 grams (98.8% yield), were substantially ash-free, whiteness being due to the light scattering caused by the pores within the beads. The porosity was confirmed by microscope examination.

EXAMPLE 3

Following the procedure of Example 2,

| | | |
|---|---|---|
| 40.0 | g. | (0.36 mole) distilled vinylpyrrolidone |
| 0.4 | g. | azobisisobutyronitrile |
| 200.0 | g. | distilled water |
| 1.2 | g. | ethylene glycol dimethacrylate |
| 0.5 | g. | 10% by weight $Na_2HPO_4$ solution |
| 33.0 | g. | anhydrous sodium sulfate | were charged to the resin flask and heated with stirring at a reaction temperature of 50° to 69°C for a total of 5½ hours.

The porous beads were filtered and washed with 1 gallon distilled water and dried in a vacuum oven at 45° to 50°C.

The dried white porous beads weighed 39.0 grams (94.6% yield).

EXAMPLE 4

Following the procedure of Example 2,

| | | |
|---|---|---|
| 40.0 | g. | (0.36 mole) distilled vinylpyrrolidone |
| 0.12 | g. | azobisisobutyronitrile |
| 240.0 | g. | distilled water |
| 2.0 | g. | tetraethylene glycol dimethacrylate |
| 1.0 | g. | 10% by weight $Na_2HPO_4$ solution |
| 40.0 | g. | anhydrous sodium sulfate | were charged to the resin flask and heated with stirring at a reaction temperature of 50° to 67°C for a total of 5 hours. The washed and dried porous beads weighed 39.2 g. (93.3% yield).

EXAMPLE 5

Following the procedure of Example 2,

| | | |
|---|---|---|
| 40.0 | g. | distilled vinylpyrrolidone |
| 0.12 | g. | azobisisobutyronitrile |
| 240.0 | g. | distilled water |
| 6.0 | g. | polyethylene glycol dimethacrylate |
| 2.0 | g. | 10% by weight solution of $Na_2HPO_4$ |
| 40.0 | g. | anhydrous sodium sulfate | were charged to the resin flask and heated with stirring at a reaction temperature of 50° to 68°C for a period of 5¾ hours. The washed and dried beads weighed 40.0 grams (86.9% yield).

EXAMPLE 6

Following the procedure of Example 2,

| | | |
|---|---|---|
| 40.0 | g. | distilled vinylpyrrolidone |
| 0.16 | g. | azobisisobutyronitrile |
| 132.0 | g. | distilled water |
| 1.6 | g. | p-divinylbenzene (99% purity of (Shell Oil Co.) |
| 0.14 | g. | 10% by weight $Na_2HPO_4$ |
| 35.0 | g. | anhydrous sodium sulfate | were charged to the resin flask and heated with stirring at a reaction temperature of 50° to 84°C for a period of 4.0 hours.

50 ml. methanol were added and stirred for ½ hour at 75°C then filtered and washed as before. The dried porous beads weighed 41.6 g. (100% yield).

EXAMPLE 7

Production of Copolymer of 60 parts vinylpyrrolidone 40 parts acrylamide crosslinked with divinylbenzene The following reactants were charged into a 1 liter stainless steel autoclave equipped with a 4 blade turbine type stirrer:

| | | |
|---|---|---|
| 96.0 | g. | vinylpyrrolidone |
| 8.0 | g. | divinylbenzene Dow DVB-55 (a mixture of isomers of divinylbenzene, ethyl vinylbenzene, and diethylbenzene, the total divinylbenzene content being 55.0%.) |
| 520.0 | g. | distilled water |
| 2.8 | g. | 10% by weight $Na_2HPO_4$ solution |
| 0.64 | g. | azobisisobutyronitrile |
| 140.0 | g. | anhydrous sodium sulfate |
| 64.0 | g. | acrylamide |

The autoclave was evacuated to 25 mm and the vacuum released with nitrogen. This procedure was repeated two more times. The contents of the autoclave were then heated with stirring to 90°C and held at that temperature for 3 hours. The porous beads were discharged, washed free of sodium sulfate and dried. The product yield was 151 g. (or 90% yield).

EXAMPLE 8

99 parts vinylpyrrolidone 1 part acrylimide crosslinked with divinylbenzene

The following reactants were charged with a 1 liter stainless steel autoclave and treated in a manner similar to Example 9.

| | | |
|---|---|---|
| 118.8 | g. | vinylpyrrolidone |
| 1.2 | g. | acrylamide |
| 390.0 | g. | distilled water |
| 0.5 | g. | azobisisobutyronitrile |
| 6.0 | g. | Dow DVB-55 divinylbenzene |
| 105.0 | g. | anhydrous sodium sulfate |
| 0.4 | g. | 10% by weight $Na_2HPO_4$ solution |

The copolymer was produced in a yield of 94.7%.

EXAMPLE 9

A phenolic complex containing 8-hydroxyquinoline was prepared by adding 2.96 grams of the dry porous beads of Example 1 to a solution of 2.50 grams of 8-hydroxyquinoline dissolved in 50 mls. of C. P. ethanol. The resultant slurry was mixed for approximately 19 hours, filtered, and dried under vacuum for three days. The dried polymer complex weighed 3.4 grams and was found by acid titration to contain 14.5 grams of 8-hydroxyquinoline.

EXAMPLE 10

A phenolic polymeric complex was prepared according to the process of Example 9 except that 5.0 grams of 8-hydroxyquinoline were dissolved in ethanol in lieu of 2.5 grams thereof. The dried polymer weighed 3.8 grams and the granules were found by titration to contain 23.9% 8-hydroquinoline. The gradual release of the phenolic material from the complex was demonstrated as follows:

25 grams of dry porous granules prepared according to Example 9 except that said granules contained 27.5% of 8-hydroxyquinoline, were wetted in 500 mls. distilled water and charged into a glass column. Distilled water was then pased through the resin bed at a steady rate of 10 mls. per minute. The effluent liquid was collected in 500 ml. portions and titrated for avaiable 8-hydroxyquinoline. Each fraction contained approximately 700 PPM of 8-hydroxyquinoline for the first 18 fractions (a total of 9 liters of that effluent) after which a reduction in concentration was noted due to the exhausting content of the polymer bed.

EXAMPLE 11

2.96 grams of polymer porous granules prepared according to Example 1 were slurried in a 10% solution of n-heptyl-p-hydroxybenzoate in C.P. ethanol for 19 hours, filtered and dried for 7 days in a high vacuum at 45°C. It was found that 1.44 grams of n-heptyl-p-hydroxybenzoate had been absorbed by the porous granules.

EXAMPLE 12

The following phenolic materials were complexed as in Example 10 and found to form a complex with the porous granular beads of Example 1. The phenolic materials complexed included:
phenol
nonyl phenyl
salicyclic acid
1,5-dihydroxy naphthalene
butylhydroxy anisole
2-nitrophenol
2,6-di-tert-butyl-p-cresol
4,6-dinitro-o-sec-butyl phenol
trichlorophenol
2,2'-thiobis(4,6-dichlorophenol)
4-n-hexylresorcinol
chlorotetracycline
vanillin.

EXAMPLE 13

Example 1 was repeated except for the use of N-methyl-N-vinylacetamide instead of N-vinylpyrrolidone. The product was treated as in Example 12 to produce a variety of phenolic complexes.

What is claimed is:

1. Porous granules or beads comprising a complex compound of a phenolic material containing a phenolic hydroxyl group with a water insoluble but water swellable crosslinked polymer of an N-vinyl lactam or an N-actyl-N-vinyl amide.

2. The granules or beads of claim 1 wherein the phenolic material is selected from the group consisting of 8-hydroxyquinoline, n-heptyl-p-hydroxybenzoate, 4,6-dinitro-o-sec-butylphenol, trichlorophenol, 2,2'-thiobis(4,6-dichlorophenol), N-alkyl-N-vinyl hydroxy anisole, 2,6-di-tert-butyl-p-cresol, 4-n-hexylresorcinol, and phenol.

3. A process for preparing the grnaules or beads of claim 1 which comprises complexing reacting porous granules or beads comprising said water insoluble, but water swellable, crosslinked polymer of an N-vinyllactam or an N-alkyl-N-vinyl amide with a solution of said phenolic material for a time sufficient to produce said complex compound.

4. The product of claim 1 wherein the porous granules or beads comprises a complex compound of a soluble compound containing a phenolic material selected from the group consisting of phenol; resourcinol; hydroquinone; salicyclic acid; nonylphenol; cresol; 8-hydroxyquinoline; 8-hydroxyquinoline hydrochloride; 4-nitrophenol; phloroglucinol; dichlorphene; gallic acid; 1,5-dihydroxynaphthalene; pyrogallol; catechol; hexachlorophene; o-chlorophenol; 4-chlorocresol; 3-aminophenol butyl hydroxyanisole; 2-nitrophenol; n-heptyl-p-hydroxy benzoate; 2,6-di-tert-butylcresol; 2-hydroxy-4-methoxybenzophenone-5-sulfonic acid; 2,4-dihydroxy benzophenone; 2-hydroxy-4-methoxy-benzophenone; 2,2'-dihydroxy-4,4'-dimethoxy-benzophenone; 2,2',4,4'-tetrahydroxy benzophenone; sodium 2,2'-dihydroxy-4,4'-dimethoxy-5-sulfo-benzophenone; and a water insoluble, but water swellable, [0.1 to 20% by weight] cross-linked polymer of an N-vinyl lactam monomer selected from those haing the formula

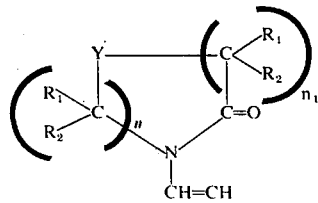

wherein $R_1$ and $R_2$ are selected from the group consisting of hydrogen, alkyl, and aryl; Y is selected from the group consisting of —O—, —S—, —$SO_2$—,

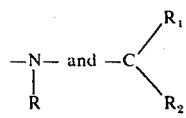

and $n$ and $n_1$ are integers from 0 to 5 provided that only one of n and $n_1$ may be zero, or a 0.1 to 20% by weight cross-linked polymer of a n-alkyl-N-vinyl-amide monomer selected from those having the formula:

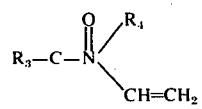

wherein $R_3$ and $R_4$ are independently a hydrocarbon radical of 1 to 4 carbon atoms; said polymers being cross-linked with between about 0.1 to about 20% by weight cross-linking agent.

* * * * *